US006916494B2

United States Patent
Park

(10) Patent No.: US 6,916,494 B2
(45) Date of Patent: Jul. 12, 2005

(54) ANTI-HEMORRHOID COMPOSITION AND PROCESS FOR ITS MANUFACTURE

(76) Inventor: Chan Sik Park, 5266 O'Faly Rd., Fairfax, VA (US) 22030

( * ) Notice: Subject to any disclaimer, the term of this patent is extended or adjusted under 35 U.S.C. 154(b) by 457 days.

(21) Appl. No.: 10/274,267

(22) Filed: Oct. 21, 2002

(65) Prior Publication Data

US 2004/0076688 A1 Apr. 22, 2004

(51) Int. Cl.⁷ .............................................. A61K 35/78
(52) U.S. Cl. ........................................ 424/725; 514/882
(58) Field of Search ........................... 424/725; 514/882

(56) References Cited

U.S. PATENT DOCUMENTS 5,466,452 A * 11/1995 Whittle ....................... 424/750

FOREIGN PATENT DOCUMENTS

KR 1998-017393 10/1998
KR 1999-0075992 10/1999

* cited by examiner

Primary Examiner—Thurman K. Page
Assistant Examiner—Sharon Howard
(74) Attorney, Agent, or Firm—Birch, Stewart, Kolasch & Birch, LLP

(57) ABSTRACT

The composition and process for preparing an anti-hemorrhoid composition which comprises providing a predetermined effective amount of natural substances of the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* in an aqueous medium to form an initial mixture, extracting the initial mixture with water at a temperature of about 70°–80° C. for 1–2 hours to produce an aqueous mixture, filtering the aqueous mixture to produce a filtrate, and evaporating the filtrate to a moisture content of 30% to produce an extract which can be used as a treatment for hemorrhoid diseases.

12 Claims, No Drawings

ANTI-HEMORRHOID COMPOSITION AND PROCESS FOR ITS MANUFACTURE

BACKGROUND OF THE INVENTION

1. Field of the Invention

The present invention relates to an anti-hemorrhoid composition made from natural substances and to a process for its manufacture. More particularly, the present invention is directed to a composition utilizing extracts of natural substances obtained from a combination of the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix*, for use in treating hemorrhoid patients, and to a process for its manufacture.

2. Description of Related Art

There are several types of known anti-hemorrhoid materials obtained from natural substances. For example, Korean Patent No. 0173393 discloses an anti-hemorrhoid composition comprising mugwort, Yin Yange Huo and buckwheat flour in an amount of 10:10:1.5% by weight. The process comprises the steps of mixing together 10 g of mugwort and 10 g of Yin Yange Huo, heating the initial mixture with 500 ml of water at a temperature of 100° C. for 30 minutes to produce 200 ml of an extract, and combining 200 ml of the extract with 1000 ml of salt water to finally producing a liquid extract which can be applied to the anus. Korean Patent Laid-Open No. 1999-0075992 discloses anti-hemorrhoid composition comprising the yellow of egg and salt. The process comprises the steps of separating the yellow part from a boiled egg, roasting the yellow of egg at a temperature of 250°–300° C. for 20 minutes, and creating an oil from the roasted yellow of egg which can be applied to the anus. However, such conventional products and processes cannot be expected to fundamentally and effectively treat hemorrhoid disease. Also, such conventional products and processes are not effective in eliminating external and internal hemorrhoids in a short period of time.

It is unknown, however, to provide an anti-hemorrhoid composition made from the natural substances of the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* in amounts of about 8.4:5.2:5.2:5.2:5.2:2.8:8.4:5.2:8.4:2.8:2.8:2.8:8.4:8.4:2.8:12.8:5.2% by weight, respectively.

Furthermore, none of the prior art processes disclose an anti-hemorrhoid extract which comprises extracts obtained from the above-identified natural substances. Accordingly, it is desirable to develop an improved composition and process for producing an anti-hemorrhoid composition for effectively treating hemorrhoidal disease and effectively relieving the itch associated with hemorrhoidal disease.

SUMMARY OF THE INVENTION

Accordingly, it is an object of the present invention to provide an anti-hemorrhoid composition obtained from natural substances and a process for its manufacture, which eliminates the above problems encountered with conventional anti-hemorrhoid compositions and methods of manufacture.

Another object of the present invention is to provide a composition utilizing an extract obtained from the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix*.

A further object of the present invention is to provide a process for manufacturing an anti-hemorrhoid extract from natural substances, such as *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* present in an amount of about 8.4:5.2:5.2:5.2:5.2:2.8:8.4:5.2:8.4:2.8:2.8:2.8:8.4:8.4:2.8:12.8:5.2% by weight, respectively.

Still another object of the present invention is to provide a medical extract of natural substances for treating and/or providing relief for a patient who has hemorrhoidal disease and/or related itch diseases.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Referring now in detail to the present invention, there is provided with an anti-hemorrhoid composition for use as a medical extract, the composition being made from natural substances, namely *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix*.

Before the extraction, a portion of the natural substances, that is, *Glycyrrhizae Radix, Rhei Rhizoma, Ephedrae Herba, Moutan Radicis Cortex, Menthae Herba, Pinelliae Rhizoma, Pasoniae Radix, Acontii Tuber, Corni Fructus, Ginseng Radix*, and *Pelladendri Radix* are preliminarily treated by washing with water to remove sand, clay, dust, and the like. After these substances are dried to a moisture content of about 5%, they are mixed together in a predetermined weight ratio and cut into a length of about 1 cm. After the preliminary treatment the balance of the natural substances listed above, that is, *Testudinis Carapax, Cervi Parvum Cornu, Natri Sulfas, Gypsum, Cinnabaris*, and *Talcum* are added to the mixture in a predetermined quantity.

In this time, the natural substances, *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* are present in an amount of about 7–9, about 4–6, about 4–6, about 4–6, about 4–6, about 2–4, about 7–9, about 4–6, about 7–9, about 2–4, about 2–4, about 2–4, about 7–9, about 7–9, about 2–4, about 11–14 and about 4–6% by weight, respectively, preferably in an amount of about 8.4:5.2:5.2:5.2:5.2:2.8:8.4:5.2:8.4:2.8:2.8:2.8:8.4:8.4:2.8:12.8:5.2% by weight, respectively.

The mixture is introduced to an extractor containing 6 times the volume of water as the mixture and soaked for about 1–2 hours at a temperature of about 70–80° C. The extracted mixture is first filtered through a centrifugal separator and then the filtrate is filtered again through a microfilter. At this time, the aromatic vapor collected in the extractor is recovered, condensed and reintroduced to the filtrate obtained from the initial mixture. The filtrate is evaporated by an automatic vacuum evaporator to a liquid content of about 30%. This concentrated liquid can be preferably administered in the form of a topical extract in order to treat or relieve hemorrhoidal disease. Also, the concentrated liquid can be dried in a dry sprayer to produce a powdered product. The powder can be formulated into a tablet form, pill form, suppository form, or ointment form, or the like in a conventional manner for use as an anti-hemorrhoidal pharmaceutical product or a health food.

In as preferred aspect of the present process, about 10% by weight of both *Glycyrrhizae Radix* and *Ginseng Radix*, respectively, are preliminary heated at room temperature for about 2 hours and in a digester prior to being added to the mixture of natural substances, in order to further improve the anti-hemorrhoidal effectiveness. It is preferred that the *Ginseng Radix* is produced in Korea.

In another embodiment of the present invention, about 1–2% by weight of other natural substances such as *Puerariae Radix, Lycii Fructus, Platycodi Radix, Angelicae Gignantis Radix, Poria Cocas Wolf, Rehmanmiae Radix, Schizandrae Fructus, Paloniae Radix, Ponciri Fructus, Nepetae Spica, Astragali Radix,* and *Coptidis Rhizoma*, respectively, can be added to the mixture in the extractor mentioned above, for further improving the anti-hemorrhoidal effectiveness of the extract composition produced by the process of the present invention.

The natural substances used by the present invention have the following ingredients. *Glycyrrhizae Radix* contains glycyrrhizin, liquiritigenin and liquiritin. *Testudinis Carapox* contains colloids, lipids and calcium salt. *Cervi Parvum Cornu* contains colloids, proteins and magnesium. *Rhei Rizoma* contains emodin, chrysophanol and rhein. *Ephedrae Herba* contains ephedrine, pseudo-ephedrine and 1-norephedrine. *Natrii Sulfas* contains $N_{a2}SO_4 10H_2O$. *Moutan Radicis Cortex* contains paeoniflorin and oxypaeoniflorin. *Paeonol Menthae Herba* contains menthol, menthone and camphene. *Pinelliae Rhizoma* contains homogentisic acid, starch and phytosterals. *Paeoniae Radix* contains paeoniflorin, oxypaloniflorin and tannin. *Acontii Tuber* contains aconitine, mesaconitine and hypaconitine. *Corni Fructus* contains marroniside, loganin and cornin. *Gysum* contains calcium sulfate. *Ginseng Radix* contains panaxadiol, panaxatrial and oleanolic acid. *Cinnabaris* contains mercury sulfate. *Talcum* contains silicon. *Pellodendii Radix* contains beberin, obakunone and obakulactone.

The present invention also includes a method of treating hemorrhoid diseases such as external hemorrhoids, internal hemorrhoids, bloody stool, anus prolapsingo, skin rashes around the anal area, and the like by administering to the mammalian recipient about 0.05 g to 0.5 g/kg body weight per day, preferably 0.07 to 0.32/kg body weight per day of the dried composition thereof.

In order for the dried composition to have maximum effectiveness in treating hemorrhoids, the dried composition should be ingested orally about 4–6 times a day, preferably 3 times between meals. The composition in a tablet composition preferably contains 0.5 g to 1.5 g of dried composition, more preferably 1 g of the dried composition.

When the composition is in the formulation of a powder, a pill, or an ointment, it will generally contain 1 g to 3 g of the dried composition.

The present invention will now be described in more detail in connection with the following examples which should be considered as being exemplary and not limiting the present invention.

EXAMPLE 1

Initially genera *Glycyrrhizae Radix, Rhei Rhizoma, Ephedrae Herba, Moutan Radicis Cortex, Menthae Herba, Pinelliae Rhizoma, Pasoniae Radix, Acontii Tuber, Corni Fructus, Gypsum, Ginseng Radix* and *Pelladendri Radix*, respectively, are washed with water to remove sand, clay, dust and the like. These natural substances are cleaned and dried to a moisture content of approximately 5%.

168 g of *Glycyrrhizae Radix*, 104 g of *Rhei Rhizoma*, 104 g of *Ephedrae Herba*, 168 g of *Moutan Radicis Cortex*, 104 g of *Menthae Herba*, 168 g of *Pinelliae Rhizoma*, 56 g of *Pasoniae Radix*, 56 g of *Acontii Tuber*, 56 g of *Corni Fructus*, 168 g of *Ginseng Radix*, and 104 g of *Pelladendri Radix* are cut into a particle size of about 1 cm and mixed together. To the mixture mentioned above are added, 104 g of *Testidinis Carapax*, 56 g of *Natrii Sulfas*, 168 g of *Gypsum*, 56 g of *Cinnabaris*, and 256 g of *Talcum*. Thereafter, this mixture is placed in an extractor having an aromatic vapor collector. 12 l of water are added to approximately 2 Kg of the mixture in the extractor. The mixture in the extractor is heated up to about 80° C. for one hour and then extracted.

The aqueous mixture is filtered first in a centrifugal separator and then is filtered again in a microfilter. The aromatic vapor distilled from the aqueous mixture is condensed and added as an aromatic liquid to the filtrate. The filtrate is evaporated through an automatic vacuum evaporator to a moisture content of about 30% to produce an extract which is useful as an anti-hemorrhoidal composition in extract form. At this time, the concentrated liquid is dried through a dry sprayer to produce a granulated formulation, a table formulation, a pill formulation, an ointment formulation, or the like, for use as an anti-hemorrhoid medicine or food.

EXAMPLE 2

The natural substances are cleaned and cut as the above Example 1. First of all, 200 g of *Glycyrrhizae Radix* and 200 g of *Ginseng Radix* produced in Korea, are preliminarily heated at a temperature of 25° C., and in a digester containing 6 times the volume of water for 2 hours. The mixture of *Glycyrrhizae Radix, Ginseng Radix* and liquid in the digester is moved to an extractor. After then, to this mixture in the extractor, 104 g of *Rhei Rhizoma*, 104 g of *Ephedrae Herba*, 168 g of *Moutan Radicis Cortex*, 104 g of *Menthae Herba*, 168 g of *Pinelliae Rhizoma*, 56 g of *Pasaniae Radix*, 56 g of *Acontii Tuber*, 56 g of *Cornii Fructus*, 168 g of *Ginseng Radix*, 104 g of *Pellodendrii Radix*, 104 g of *Testudinis Carapax*, 104 g of *Cervi Parvum Cornu*, 56 g of *Natrii Sulfas*, 168 g of *Gypsum*, 56 g of *Cinnabaris*, and 192 g of *Talcum* are added. Thereafter, the procedure of Example 1 is repeated to produce an anti-hemorrhoidal composition and food for use in treating and relieving hemorrhoid disease.

TEST EXAMPLE 1

Treatment of Bloody Stool

Chang G. Lee is a 53-year-old man weighing 70 kg was diagnosed as having chronic bloody stool, having suffered with this disease for more than twelve years. The symptoms accompanied with severe stomach pain were especially noticeable after drinking alcoholic beverages or ingesting spicy food. He was given a sixty-day Kyunghee Herb's extract treatment in two consecutive periods, with an interval of fifteen days between them. During the first half of the procedure, four tablets were given each day, each between the meals. It was noted that the bloody stool and stomach pain was considerably reduced after the first half of the procedure. After sixty days, both the bloody stool and the stomach pain disappeared.

TEST EXAMPLE 2

Treatment of Prolapsing of Anus

Chun H. Kim is a 54-year-old man weighing 73 kg, who was diagnosed with severe hemorrhoids along with prolapsing of the anus for fifteen years. After he tried the Kyunghee Extract for one month, he experienced relief and after drinking the extract for four months, he was completely healed of the hemorrhoids.

TEST EXAMPLE 3

Treatment of Skin Rashes around the Anal Area

Jung O. Ahn is a 52-year-old woman weighing 50 kg, who had obtained no relief from various types of treatment for her rashes around the anal area, she took Kyunghee Herb's ointment and extract. She used the Kyunghee Herb's ointment both as an anti-itching external lotion, and as an extract administered internally, for two months. During the first two weeks of the period, the skin rashes began to decrease. After two months, her itching went away and she is now living a normal life without complications.

TEST EXAMPLE 4

Treatment of Severe Skin Rashes Around the Anal Area

Jae H. Lee is a 23-year-old man, weighing 65 kg, who has had severe skin rashes around the anal area since childbirth. It has been difficult for him to walk or even sit down. After he took Kyunghee Herb's tablets for three months, he had completely cured his hemorrhoidal problems.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An anti-hemorrhoid composition comprising a pharmaceutically effective amount of an extract of the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix*.

2. The anti-hemorrhoid composition of claim 1, wherein

*Glycyrrhizae Radix* is present in an amount of about 7–9% by weight,

*Testudinis Carapax* is present in an amount of about 4–6% by weight,

*Cervi Parvum Cornu* is present in an amount of about 4–6% by weight,

*Rhei Rhizoma* is present in an amount of about 4–6% by weight,

*Ephedrae Herba* is present in an amount of about 4–6% by weight,

*Natrii Sulfas* is present in an amount of about 4–6% by weight,

*Moutan Radicis Cortex* is present in an amount of about 2–4% by weight,

*Menthae Herba* is present in an amount of about 7–9% by weight,

*Pinelliae Rhizoma* is present in an amount of about 4–6% by weight,

*Pasoniae Radix* is present in an amount of about 7–9% by weight,

*Acontii Tuber* is present in an amount of about 2–4% by weight,

*Corni Fructus* is present in an amount of about 2–4% by weight,

*Gypsum* is present in an amount of about 2–4% by weight,

*Ginseng Radix* is present in an amount of about 7–9% by weight,

*Cinnabaris* is present in an amount of about 7–9% by weight,

*Talcum* is present in an amount of about 11–14% by weight, and

*Pelladendri Radix* is present in an amount of about 4–6% by weight.

3. The anti-hemorrhoid composition of claim 1, wherein

*Glycyrrhizae Radix* is present in an amount of about 8.4% by weight,

*Testudinis Carapax* is present in an amount of about 5.2% by weight,

*Cervi Parvum Cornu* is present in an amount of about 5.2% by weight,

*Rhei Rhizoma* is present in an amount of about 5.2% by weight,

*Ephedrae Herba* is present in an amount of about 5.2% by weight,

*Natrii Sulfas* is present in an amount of about 2.8% by weight,

*Moutan Radicis Cortex* is present in an amount of about 8.4% by weight,

*Menthae Herba* is present in an amount of about 5.2% by weight,

*Pinelliae Rhizoma* is present in an amount of about 8.4% by weight,

*Pasoniae Radix* is present in an amount of about 2.8% by weight,

*Acontii Tuber* is present in an amount of about 2.8% by weight,

*Corni Fructus* is present in an amount of about 2.8% by weight,

*Gypsum* is present in an amount of about 8.4% by weight,

*Ginseng Radix* is present in an amount of about 8.4% by weight,

*Cinnabaris* is present in an amount of about 2.8% by weight,

*Talcum* is present in an amount of about 12.8% by weight, and

*Pelladendri Radix* is present in an amount of about 5.2% by weight.

4. The anti-hemorrhoid composition of claim 1, wherein
*Glycyrrhizae Radix* is present in an amount of 10% by weight,
*Testudinis Carapax* is present in an amount of 5.2% by weight,
*Cervi Parvum Cornu* is present in an amount of 5.2% by weight,
*Rhei Rhizoma* is present in an amount of 5.2% by weight,
*Ephedrae Herba* is present in an amount of 5.2% by weight,
*Natrii Sulfas* is present in an amount of 2.8% by weight,
*Moutan Radicis Cortex* is present in an amount of 8.4% by weight,
*Menthae Herba* is present in an amount of 5.2% by weight,
*Pinelliae Rhizoma* is present in an amount of 8.4% by weight,
*Pasoniae Radix* is present in an amount of 2.8% by weight,
*Acontii Tuber* is present in an amount of 2.8% by weight,
*Corni Fructus* is present in an amount of 2.8% by weight,
*Gypsum* is present in an amount of 8.4% by weight,
*Ginseng Radix* is present in an amount of 10% by weight,
*Cinnabaris* is present in an amount of 2.8% by weight,
*Talcum* is present in an amount of 9.6% by weight, and
*Pelladendri Radix* is present in an amount of 5.2% by weight.

5. The anti-hemorrhoid composition of claim 1, wherein the extract further contains about 1–2% by weight of extracts of *Puerariae Radix, Lycii Fructus, Platycodi Radix, Angelicae Gignantis Radix, Poria Cocas Wolf, Rehmanmiae Radix, Schizandrae Fructus, Paloniae Radix, Ponciri Fructus, Nepetae Spica, Astragali Radix* and *Coptidis Rhizoma*.

6. A process for preparing an anti-hemorrhoid composition which comprises:
(a) mixing together a pharmaceutically effective amount of the natural substances of the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix*, in an aqueous media to form an initial mixture,
(b) extracting said initial mixture with water at a temperature of about 70°–80° C. for about 1–2 hours to produce an aqueous mixture,
(c) filtrating said aqueous mixture to produce a filtrate, and
(d) evaporating said filtrate down to a moisture content of about 30% to produce a medicinal extract.

7. The process of claim 6, wherein the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* are present in an amount of about 7–9, about 4–6, about 4–6, about 4–6, about 4–6, about 2–4, about 7–9, about 4–6, about 7–9, about 2–4, about 2–4, about 2–4, about 7–9, about 7–9, about 2–4, about 11–14 and about 4–6% by weight, respectively.

8. The process of claim 7, wherein the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* are present in an amount of about 8.4%, about 5.2%, about 5.2%, about 5.2%, about 5.2%, about 2.8%, about 8.4%, about 5.2%, about 8.4%, about 2.8%, about 2.8%, about 2.8%, about 8.4%, about 8.4%, about 2.8%, about 12.8% and about 5.2% by weight, respectively.

9. The process of claim 6, wherein the genera *Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris, Talcum* and *Pelladendri Radix* are present in an amount of about 10%, about 5.2%, about 5.2%, about 5.2%, about 5.2%, about 2.8%, about 8.4%, about 5.2%, about 8.4%, about 2.8%, about 2.8%, about 2.8%, about 8.4%, about 10%, about 2.8%, about 9.6% and about 5.2% by weight, respectively.

10. The process of claim 6, wherein the genera *Glycyrrhizae Radix* and *Ginseng Radix* are preliminarily heated in a digester at a room temperature for about 2 hours prior to being mixed with the other natural substances.

11. The process of claim 6, wherein the extracting is conducted at a temperature of about 80° C. for about one hour.

12. The anti-hemorrhoid composition comprising an extract produced by the process of claim 6.

* * * * *